United States Patent [19]

Huffstutler, Jr. et al.

US005466455A

[11] Patent Number: 5,466,455

[45] Date of Patent: * Nov. 14, 1995

[54] POLYPHASE FLUID-EXTRACTION PROCESS, RESULTING PRODUCTS AND METHODS OF USE

[76] Inventors: Miles C. Huffstutler, Jr., 1608 W. 155th St., Burnsville, Minn. 55306; Gary M. Steuart, P.O. Box 356, Harmony, Minn. 55939

[*] Notice: The portion of the term of this patent subsequent to Jul. 19, 2011, has been disclaimed.

[21] Appl. No.: 120,988

[22] Filed: Sep. 15, 1993

Related U.S. Application Data

[63] Continuation-in-part of Ser. No. 980,839, Nov. 24, 1992, Pat. No. 5,330,756, which is a continuation-in-part of Ser. No. 599,616, Oct. 18, 1990, abandoned.

[51] Int. Cl.⁶ .......................... A61K 35/78; A01N 25/02
[52] U.S. Cl. .................. 424/401; 424/45; 424/47; 424/195.1; 424/450; 424/DIG. 15
[58] Field of Search .................................. 424/401, 405, 424/450, 43, 44, 45, 46, 47, 195.1, 433, 443, DIG. 15; 514/965, 937; 264/4; 436/829

[56] References Cited

U.S. PATENT DOCUMENTS 4,670,263  6/1987  Noorlander .................... 424/195.1

*Primary Examiner*—Thurman K. Page
*Assistant Examiner*—Carlos Azpuru
*Attorney, Agent, or Firm*—M. Conrad Huffstutler

[57] ABSTRACT

Processes for polyphase fluid extraction of concentrated, active therapeutic components from parts of selected medicinal plants which have been identified chemotaxonomically are described. The resulting products-by-processes are defined as Concentrated Fluid Therapeutic Extracts, CFTE, of the selected plant types, where T represents a specific herbal plant family such as Symphytum, SYM, Taxus, TAX, Panax, PAN or Aloe, ALO. The process disclosed for CFTE preparation includes multiple/sequential stages of diffusional transfer of bioactive constituents from plant tissue into liquid and/or vapor extraction phases under contact conditions of forced convection at controlled temperature and pressure. Therapeutic formulations based on CFTE including emulsions, aerosols, liposomes and controlled-release devices are presented. Treatment methods for a variety of mammalian diseases and conditions and complications of specific diseases are described.

15 Claims, No Drawings

POLYPHASE FLUID-EXTRACTION PROCESS, RESULTING PRODUCTS AND METHODS OF USE

RELATED APPLICATION

This application is a continuation-in-part of U.S. Ser. No. 07/980839, filed Nov. 24, 1992, now U.S. Pat. No. 5,330,756, which is a continuation-in-part of U.S. Ser. No. 07/599,616, filed Oct. 18, 1990, now abandoned.

BACKGROUND OF THE INVENTION

1. Technical Field

This invention relates to medicaments containing Concentrated Fluid (CF) extracts from tissues derived from various plant species particularly those which have been chemotaxonomically identified as a species of Agauria, Artemenisia, Camellia, Galphimia, Notopterygium, Pisum, Phyllanthrus, Rhodendron, Taxus, Panax, Ginko, Symphytum, Aloe and Waldstenia. The invention also covers tissue propagated by any means, including culturing of callus cells and optimal horticultural/harvesting methods and polyphase fluid-extraction processes for recovery of bioactive plant secretions such as phytoalexins which result from immediate, optimized processing of freshly-harvested plant tissues. The invention also covers processes for innoculating living plants or cultured tissues derived from herbal plants with endophytic organisms, i.e., symbiotic parasites such as yeasts, fungus, etc. for the purpose of increasing the total amount of extractable, bioactive components. The invention also covers preparation of mammalian medicaments in various forms including oral, topical, parenteral, transdermal, transmucosal, aerosol, liposomes, suspensions, emulsions, etc. The invention also covers methods for use of the several medicaments and forms for therapy on humans and other mammals.

2. General Background
A. Traditional Chinese Herbal Remedies

Classic Chinese herbal medicine references report soaking, under room conditions (approx. 20 C, and 100 kPa, in an air environment), of dried leaves or roots of many herbal plants. A few modern scientific studies have identified saponins, galactosides, polysaccharides, etc. as being present in herbal cures derived from plant parts of unknown age and dried by various methods; the usual purpose of such studies is to compare clinical testing results of "Chinese herbal extracts" with modern synthetic drug compounds. Remarkably, no reference could be found for harvesting herbal plants at a specific stage of growth/maturity into closed protective vessels for immediate processing/ extraction. According to Chinese tradition, slow air drying in full sunlight is a typical part of the procedure. Liquid-nutrient-media and cell-culture methods for plant cells cannot be found in any reference work for homeopathic medicine. No references can be found to studies of selective breeding and horticulture of herbal plants to maximize either: (a) the levels of bioactive constituents in their tissue just prior to harvest or (b) the amount and number of bioactive constituents generated/secreted by the tissue of herbal plants in response to specific preextraction processing steps such as mechanical injury to cell walls, e.g., by comminuting plant tissue to a selected size range. This is not unexpected, since the basic research in the fields of chemotaxonomy, herbal-plant genetics, and plant-tissue response to injury or other stress is now in its infancy.

B. CF Taxus Extracts, CFTAXE

Taxines, baccatins, and taxol are the principal medicinal constituents which can be extracted from tissue and plant elements of species identified chemotaxonomically as *T. baccata, T. brevifolia, T. canadensis, T. chinesis, T. cuspidata, T. floridana* and other wild or non- wild types. Extractable plant elements include flowers, seeds, needles, leaves, buds, nuts, cones, blooms, branches, stems, bark, phloem-cambrial layer and roots. The alkaloids in extracts are poisonous to humans and animals if taken internally; typical symptoms include GI irritation, and failure of circulatory and respiratory functions. Experimental parenteral "taxol" preparations (developed by chemical modification and synthesis) are also believed to be useful, along with other known radiation and chemotherapy technics, for treatment of certain tumors. Since 1989, EPA and environmental groups have targeted firms harvesting bark from the Pacific yew for protests and legal actions; these disputes have essentially halted research on yew-bark-derived taxol in USA.

No publications on: (a) poly- phase, fluid- extraction processes or (b) fine-disperse mammalian therapeutic forms can be found for extracts of plant tissue derived from any Taxus- type plant.

C. CF Aloe Extracts, CFALOE

Aloin, is the principal medicinal constituent of thickened, leaf- cell fluid of Aloe species identified chemotaxonomically as *A. perryi,* or *A. vera* and other wild or non- wild types; the other constituents include resin, emodin and a mixture of volatile oils. Extractable plant components include flowers, seeds, leaves, anthers, buds, blooms, stems and roots. Aloin isolates administered orally are known for cathartic and purgative use. According to the lore of herbal medicine, "aloe extacts" are useful for skin care and moisturization.

No publications on: (a) poly- phase, fluid- extraction processes or (b) fine-disperse mammalian therapeutic forms can be found for extracts of plant tissues derived from any Aloe- type plant.

D. CF Panax Extracts, CFPANE

Curative powers of ethanol extracts of dried roots of Panax species such as *P. japonicus, P. notoginseng, P. shinseng,* and *P. quinquefolium* have been known for many years in the lore of folk medicine from China, Japan and Korea. According to some Oriental practitioners, Panax-based healing formulations prepared by traditional practice can be used to treat most maladies known to man.

No publication can be found which describes Panax plant, or plant-tissue, culture/breeding/harvesting, Panax cultivars/ hybrid species, *Panax chemotaxonomy;* no literature can be found on optimization of any of these factors for preparation of medicaments based upon bioactive species extracted from freshly-harvested Panax plant tissues including, leaves, roots, stems, petioles, buds, flowers, pollen, callus cells, etc. Similarly, no publication can be found which describes sophisticated harvesting methods/timing for maximum yield of therapeutic constitients from Panax tissue such as roots, rhizomes, or rootlets/hairs. Likewise no publication can be found which describes preservation of therapeutic constituents against degradation and oxidation during drying of any plant tissue. Further, no publication can be found on processing or extraction of freshly-harvested Panax plant tissues in a controlled environment with liquid and vapor-phase fluids.

E. CF Symphytum Extracts, CFSYME

Ethanol or propylene glycol extract solutions of "dried comfrey roots and leaves" are known wound-healing agents as used in topical preparations. As with all medicinal or herbal plants, the actual chemical constituents of in-vivo plant parts are highly dependent upon the genome, plant maturity at harvest, available soil moisture and nutrients, and environmental factors such as infestation by fungus/ insects, pollution and climate parameters such as growth-season degree days and freedom from disease, fungus and insect infestation. Classic herbal medicine references give no definite values for the actual level of specific or identified active components in the resulting extracts; neither do they give any indications as to the probability of dangerous impurities and contaminants which may also be present. Indeed, the recipes for "comfrey poultices, plasters, and curative teas" typically do not even confirm the solubility of "active components" in the actual extract solvent solution at any temperature. No references can be found for liquid-nutrient, cell-culture methods for propagation of Symphytum tissue and recovery of bioactive components.

This continuing and profound lack of specificity concerning how to grow and harvest selected plant types, which plant parts to extract, how to do the extraction to get optimal or efficient therapeutic concentrations is no doubt responsible for the various "comfrey" controversies such as poisoning of humans and animals due to pyrrolizidine alkaloids. For products marketed in USA, the FDA has determined that no therapeutic claims can be made for any old-type "comfrey" compositions which have not been subjected to comprehensive lab/animal/and clinical validations according to detailed IND and NDA procedures.

F. CFTE Extracts From Other Plant Species.

Ethanol extracts of dried roots and leaves of other herbal species including Artemenisia, Camellia, Galphimia, Ginko, Notopterygium, Phyllanthrus, Rhodendron, Teucrium and Waldstenia are portrayed to have various curative and prophylactic properties according to traditional Chinese folk medicine. As already noted above in the case of Panax, no scientific literature is available on cell-culture propagation, plant breeding, optimal horticulture methods, improved harvesting methods/systems, rationalized extraction for freshly-harvested plant elements, modern drug formulations and fine-dispersed physical forms of medicaments, e.g., liposomes, aerosols, emulsions, transdermal patches which have superceded traditional plasters and poultices.

SUMMARY OF THE INVENTION

The main object of this invention is the preparation of Concentrated Fluid Therapeutic Extracts, CFTE, are prepared for therapeutic use by means of single or polyphase extraction in a closed, controlled environment from comminuted, plant tissue processed under controlled environment from harvesting. Single-phase extraction means that a fluid in the liquid or the gas phase contacts the plant tissue to be extracted. Polyphase extraction means more than one phase of an extract fluid will be present in the extraction environment, either simultaneously or chronologically, i.e., sequentially by the condensation of a vapor phase under pressure to produce a liquid phase.

For the purpose of this specification and claims, CFTE are defined as therapeutic extracts containing those bioactive substances which can be:

(a) generated within and recovered from freshly-havested plant tissues, including at least one of the plant elements comprising flowers, seeds, leaves, anthers, callus cultures, buds, blooms, pollen, petioles, stems and rhizomes, roots, of any one or more wild or non- wild species including *Agauria salicifolia, Albizia amara, Allium sativum, Anemarrhena asphodeliodes, Archangelica officinalis, Artemenisia annua, Artemisia annua, Aster scaber, Azadirachta indica, Bixa orellana, Bryophyllium pinnatum, Bupleuri radix, Calophyllum lanigerum,* Calubrina (mabi), *Camellia sinesis* (green tea), *Cassia alata, Coccinia indica, Dallium guincese, Desmos chinensis,* Eleutherococcus, *Eleutherococcus senticosus, Ephedra sinica, Erythrina costaricensis, Fusarium acuminatum, Galphimia glauca, Gardeniae fructus, Ginko bilboa, Glycrrhizae radix, Himanthalia elongata, Hypericum perforatum, Ipomoea tricolor, Jatropha curcas, Kigelia pinnata, Lactocuccus lactis, Lathyrus sativus, Ledum palustre, Lepechinia hastata, Mentha arvensis, Mirabilis jalapa, Momordica charantia, Notopterygium forbesii, Notopterygium incisium, Ocimum gratissimum, Origanum cordifolium, Panax japonicum, Panax japonicus, Panax notoginseng, Panax quinquefolium, Panax shinseng, Parietaria judaica, Phoenix dactylifera, Phyllanthrus amarus, Phyllanthrus maderapatensis, Picrorhiza kurroa, Piper methysticum, Pisum sativum, Plumbago rosea, Policias fruticosum* (Dihn-lang), *Pongamia pinnata, Psidium guajava, Rhododendron luteum, Rhododendron ponticum, Rosmarinus officinalis, Salvia officinalis, Saraka asoca, Slavia miltiorrhzia, Symphytum officinale, Symphytum asperum, Symphytum armeniacum, Symphytum tauricum, Symphytum sylvaticum, Symphytum peregrinum, Symphytum anatolicum, Symphytum icaricum, Symphytum orientale, Symphytum kurdicum, Symphytum pseudobulbosum, Symphytum uplandicum, Symphytum circinale, Symphytum ottomanum, Symphytum icaricum, Symphytum brachycalyx, Symphytum aintabicum, Symphytum longisetum, Symphytum bornmuelleri, Symphytum tuberosum, Symphytum bulbosum, Symphytum ibericum,* or *Symphytum longipetiolatum, Teucrium cyprium, Teucrium divaricatum_canescens, Teucrium micropdioides, Veronia amygdalina, Waldstenia fragarioides* harvested at the optimum stage for the particular plant part, i.e., peri-bloom for leaves and blooms or sprouting for roots/rhizomes, and (b) extracted in a controlled or recirculated environment with poly-phase fluids from whole tissue or comminuted particles of any or all of the above-named plant-tissues at temperatures in the range of 20–400 deg. K with an extractant- fluid contact interval of 0.1 to 200 hours and with starting input weight ratios of extract fluid/plant tissue of 0.01/1 up to 10000/1.

According to this definition, the fluid may be initially a vapor phase which permeates into the plant elements and will under equilibrium conditions and then nucleate and condense one or more liquid phases on and within the plant-tissue elements. Further, according to this invention the fluid may initially contain medical- type surfactants which enhance its capillary flow within the structure of the plant tissue. Further according to this definition, the types of defined contact between the plant elements and the extracting fluid include gravity flow of a liquid condensate, gravity drainage of a liquid fluid sprayed from the upper zones of the reactor, circulation/fluidization by means of vapor phase with or without a dispersed equilibrium aerosol and forced convection circulation/fluidization by means of a liquid fluid. For such flow variations, the forced-convection- contact- velocity differential would fall in the range 0.01 to 10 meters/sec. Still further according to this definition, the defined extraction environment includes inert gases and/or condensable vapor phases in the range of pressures from 1 to 10000 kPa and temperatures in the range 20–400 deg. K. Since certain bioactive components and precursors are only sparingly soluble in aqueous solutions, other fluid-solvents must be used for poly-phase extraction; these include alcohols, ethers, ketones, acetonitrile, toluene, etc. Further, polyphase fluids may include emulsions of immiscible liquids such as droplets of a liquid organic solvent in a continuous phase of liquid water or an aqueous solution.

Another general object of the present invention is to provide new, improved therapeutic formulations and compositions of CFTE, especially CF Symphytum Extracts, CFSYME, which can be used for dermatological treatment of a number of skin and mucosal membrane conditions in humans and animals. These conditions include but are not limited to: skin dryness/allergies/rashes, tissue healing, prevention of scaring complications, fungal infections, treatment of minor burns, etc.

The invention includes various physical forms of CFSYME formulations (emulsions, liposomes, aerosols) which are not available commercially or reported in the scientific literature. It is believed that the bioavailability of CFSE is enhanced in fine- dispersed forms relative to typical bulk-solution forms.

The invention includes therapeutic and dermatological formulations in various physical forms with high concentration levels of CFSYME e.g., higher than any known "comfrey" preparations or published "comfrey" treatment protocols. Liquid preparations according to this invention contain CFSYME components in excess of 0.02 wt. % of the total weight of the final preparation as used. The use of such enriched formulations according to this invention, thus allows smaller quantities of the preparation to be used to deliver the same amount of active components of the Symphytum extract.

For emulsion-type formulations, this invention includes topical CFSYME consisting of O/W emulsions, oil being the dispersed phase and water the continuous phase, for the purpose of protecting, moisturizing, and stimulating the healing processes of skin or mucous membrane.

Skin-treatment O/W emulsion formulations according to this invention contain selected oils for moisturizing the skin, especially the stratum corneum and high levels of CFSYME in the water phase for maximal healing properties.

This invention also includes improved methods for use of CFSYME formulations in alternative physical forms including liquid emulsions such as foam, spray, gel, lotion, cream, ointment, and dispersed vesicles, particles or droplets solid- or liquid-aerosols, liposomes, microemulsions, for maximum effectiveness in wound healing.

This invention includes new methods for controlled-release of CFSYME impregnated into a fibrous matrix or blended with an adhesive.

Patients with AIDS usually experience skin breakdown problems, e.g., folliculitis, "itchy red bumps", psoriasis, and dry itchy skin. Topical emulsion preparations of CFSYME according to this invention significantly relieve the itching in many cases and help promote healthier skin.

Healthcare workers—because of frequent hand washing and wearing surgical gloves —often experience dermatitis, i.e., severe chapping and dryness of the skin. Topical emulsion-type CFSYME formulations according to this invention reduce dryness and, in many cases, stimulate healing to point that the skin becomes healthy again. Similarly, workers who are exposed to irritating substances in their occupation can use similar CFSYME/formulations for either therapeutic or prophylactic purposes.

Diabetic patients often experience dry skin and in some cases stasis ulcers which heal with difficulty. Topical emulsion-type CFSYME formulations according to this invention help relieve the dryness and in some cases has proven to be a good healing agent for the stasis ulcers.

Paraplegics or bedridden patients can experience pressure sores or decubitus ulcers. Topical emulsion-type CFSYME formulations according to this invention help condition the skin and thus prevent the formation of the ulcers. Further, the formulations will stimulate the healing of those ulcers already extant.

Other uses for emulsion- type CFSYME formulations according to this invention include: diaper rash, chapped or dry skin, sunburn, insect bites, minor wounds, cold sores, athlete's foot, and minor burns.

A secondary objective of this invention is the preparation and use of therapeutic compositions containing CF Taxus Extracts, CFTAXE, for treatment various forms of malignant disorders, cell- proliferative diseases and carcinomas. Specific extraction processing parameters fall in the ranges noted above for CFSYME. This invention also includes improved methods for use of CFTAXE formulations in alternative physical forms including liquid emulsions, foam, spray, gel, lotion, cream, ointment, and dispersed vesicles, particles or droplets solid- or liquid-aerosols, liposomes, microemulsions, for maximum effectiveness in treatment of carcinomas, cell- proliferative diseases and malignant disorders. This invention includes new methods for controlled-release of CFTAXE impregnated into a porous/fibrous matrix or blended with an adhesive.

A tertiary objective of this invention is the preparation and use of therapeutic compositions containing CF Aloe Extracts, CFALOE, for skin injuries/burns, inflammations, infections, and diseases. Specific extraction processing parameters fall in the ranges noted above for CFSYME. This invention also includes improved methods for use of CFALOE formulations in alternative physical forms including liquid emulsions, foam, spray, gel, lotion, cream, ointment, and dispersed vesicles, particles or droplets solid- or liquid-aerosols, liposomes, microemulsions, for maximum effectiveness in treatment of skin diseases, injuries, inflammations, and allergies/sensitizations. This invention includes new methods for controlled- release of CFALOE impregnated into a porous/fibrous matrix or blended with an adhesive.

Another objective of this invention is the preparation and use of therapeutic compositions containing CF Panax Extracts, CFPANE for ingestion, delivery by implant and parenteral injection. Bioactive therapeutic agents from Panax are useful for treating tumors, anemia, myocardial circulation, cerebral ischemia as well as preventing free-radical damage and platelet aggregation. This invention also includes improved methods for use of CFPANE formulations in alternative physical forms including liquid emulsions, foam, spray, gel, lotion, cream, ointment, and dispersed vesicles, particles or droplets solid- or liquid-aerosols, liposomes, microemulsions, for maximum effectiveness in treatment of various diseases and injuries. This invention includes new methods for controlled- release of CFPANE impregnated into a porous/fibrous matrix or blended with an adhesive.

BEST MODES FOR CARRYING OUT THE INVENTION

The best mode for preparation of a CF Therapeutic Extract starting from freshly-harvested plant tissue involves selection of tissue which has been propagated and harvested under controlled conditions so that it contains at harvest, or is able to secrete during processing, especially comminution, bioactive species. These criteria are met by using principles of chemotaxonomy to validate the genome of original plant stock as a useful source of the desired bioactive components, irrespective of whether the plant tissue is propagated by horticultural or cell-culture methods. In the case of species such as Taxus, which produce bioactive agents as a result of a parasitic endophytic fungal infestation, the tissue to be harvested may require innoculation with the the desired fungus prior to harvest so that its own tissue-defensive secretions, as well as the toxins secreted by the fungus, are present at economically-useful levels, and can be recovered by immediate poly-phase extraction of the tissue. The use of multiple fluid phases as taught by this invention allows optimal extraction of bioactive components, i.e., the several therapeutic agents are partitioned into more than one solvent phase or fluid according to their solubility in that specific fluid phase. By the use of low-temperature initial-processing fluids such as liquified pure gases or gas mixtures, the bioactive agents can be preserved within the cells/cell membranes by rapid supercooling immediately after harvest so that with cell walls are not ruptured by slow-growing water-ice crystals as occurs when the plants freeze on a cold night. Combined with a sequential, i.e., later rewarming extraction-process step, the tissue may be preserved for an extended period at temperatures below about 250 deg. K; this would be an example of an interrupted-sequential extraction in poly-phase fluids. Contact of 1 mm-size fragments/particles of freshly-harvested tissue with a biocompatible liquid fluid at temperatures in the range 20 to 250 deg. K is a useful in-field cryopreservation step or the initial stage of a sequential poly-phase extraction.

One preferred formulation of this invention is an O/W emulsion with at least 0.02 wt. % of active components within CFSYME prepared as described in the following.

CF Symphytum Extract preparation. Preferably, fresh Symphytum leaves/stems are used, and at least 60 grams of leaves/stems are comminuted into one liter of liquid aqueous extracting fluid. Alternatively CF Symphytum Extract is made by comminuting at least 6 grams of process-dessicated Symphytum leaves, stems or roots and combining the particles with one liter of liquid aqueous extracting fluid. In this context, "process-dessicated" denotes less than 10 wt. % water, on an absolute or "bone-dry" basis, and the processes for dessication can include freeze drying, drying by solvents which remove water without rupturing cells and drying by the use of vapors of low-boiling fluids to facilitate water removal from the plant tissue. The forced- convection-contact- velocity differential for the process should be in the range 0.01 to 10 meter/sec.

For another preferred embodiment, the extracting fluid may be an undiluted or "neat" liquid such as glycerol, ethanol, water, methylene chloride and the chamber environment is the equilibrium vapor of the liquid at the selected temperature, i.e.,a pressure of about 100 kPa. Alternatively, the extract fluid may be a liquid solution or two-phase emulsion. The extraction process requires approximately 72 hours contact at temperatures between 20 and 30 deg. C. The forced- convection-contact- velocity differential for the process should be in the range 0.01 to 10 meter/sec. The supernatant extract is filtered thru typical food-type paper filters (nominal pore size 10–100 micrometers).

In the case of extraction with a physiologically- compatible solution (generally isotonic to blood and tissue, 250–350 mOsm/kg), the filtrate may be used directly to prepare final liquid formulations for use in intravenous, subcutaneous, intramuscular, intralymphatic, intraperitoneal, or intraplueral preparations.

Alternatively, the filtrate may be evaporated to reduce the extractant to as little as zero %. To facilitate preparation of certain formulations or physical forms, the extraction step can be done with water or aqueous solutions containing a reduced level of physiologic components (such as saline) and the final adjustment to physiologic osmolality range being accomplished by addition of specific concentrates to the filtered CF Symphytum Extract.

The concentrated filtrate can be added directly to the water phase or it can be resuspended with an alternative vehicle , e.g. water, or glycerol. One kilogram of the final formulation contains CF Symphytum Extract from at least 60 grams of freshly-harvested leaves/stems or the extract from at least 12 grams of freshly-harvested roots.

In typical O/W emulsions, the volume percent of the dispersed phase is in the range of 0.1–25 vol. %. For these formulations, the major quantity of CF Symphytum Extract is contained in the water-solution phase of the emulsion, whether it is a simple O/W emulsion or a complex W/O/W emulsion wherein water is the continuous phase and the primary dispersed phase is oil droplets which in turn contain smaller droplets of the continuous phase, water. W/O/W dispersions may also be called double or multiple emulsions.

Liposome dispersions of CFSYME can be made spontaneously by the technique of adding a quantity of aqueous extract solution to a dry film of lipid or phospholipid. Other known alternative methods of forming liposomes such as injection, reverse-micelle formation and reverse-phase evaporation can also be used to produce liposomes from aqueous CFSYME. The therapeutic characteristics of the resulting vesicles can be tailored for specific diseases or tissue applications by: (a) altering the average diameter/size of the vesicle, (b) altering the surface charge of the vesicle, (c) altering the stiffness of the encapsulating vesicle membrane-film and (d) incorporation of antibodies or ligands into the vesicle surface/film which show binding or affinity for specific types/forms of tissue.

Aerosol dispersions of solid- or liquid- phase CFSYME can be made by techniques such as atomization, nebulization, spray drying, freeze drying.

CFTAXE Extraction Technics.

fluid type: water, C1–C10 alcohols, C1–C3 ketones, C1–C4 acetates, C1–C4 ethers, C1–C3 halocarbons, acetonitrile, toluene, and solutions/dispersions thereof with liquid and/ or vapor phases pressure range: 0.1X < vapor pressure of most-volatile fluid component at maximum extraction temperature in cycle, kPa < 20X temperature range: 20–400 deg. K mass-transport parameters:

0.01/1< weight ratio input plant tissue/extract <10000/1

0.01< forced-convection-contact-velocity differential, meter/sec <10 total diffusional contact time: 1< cycle time, hours <200

CFTAXE Formulations and Use Technics

A wide variety of CFTAXE formulations can be made; these include topical, transdermal, transmucosal, parenteral compositions in fluid- forms i.e., solutions, suspensions, emulsions, and fine- disperse forms such as foams, liposomes, vesicles, micelles and aerosols. Known pharmaceutical excipients appropriate to the specific administration mode and use-form can be blended with CFTAXE. For therapy of carcinomas and malignant disorders, parenteral forms of CFTAXE can be used; however, targeted liposome formulations adapted for breast or uterine tumor treatment are preferred.

CFALOE Extraction Technics.

fluid type: water, C1–C10 alcohols, C1–C3 ketones, C1–C4 acetates, C1–C4 ethers, C1–C3 halocarbons, and solutions/dispersions thereof with liquid and/or vapor phases pressure range: 0.1X < vapor pressure of most-volatile fluid component at maximum extraction temperature in cycle, kPa <20X
temperature range: 20–400 deg. K
mass-transport parameters:
0.01/1< weight ratio input plant tissue/extract <10000/1
0.01< forced-convection-contact-velocity differential, meter/sec <10 total diffusional contact time: 1< cycle time, hours <200

CFALOE Therapeutic Formulations and Use Technics

A wide variety of CFALOE formulations can be made; these include topical, transdermal, transmucosal, parenteral compositions in fluid- forms i.e., solutions, suspensions, emulsions, and fine- disperse forms such as foams, liposomes, vesicles, micelles and aerosols. Known pharmaceutical excipients appropriate to the specific administration mode and use-form can be blended with CFALOE.

CFPANE Extraction Technics
CFPANE Extraction Technics.
fluid type: water, C1–C10 alcohols, C1–C3 ketones, C1–C4 acetates, C1–C4 ethers, C1–C3 halocarbons, acetonitrile, toluene, and solutions/dispersions thereof with liquid and/or vapor phases
pressure range: 0.1X < vapor pressure of most-volatile fluid component at maximum extraction temperature in cycle, kPa <20X
temperature range: 20–400 deg. K
mass-transport parameters:
0.01/1< weight ratio input plant tissue/extract <10000/1
0.01< forced-convection-contact-velocity differential, meter/sec <10 total diffusional contact time: 1< cycle time, hours <200

CFPANE Therapeutic Formulations and Use Technics

A wide variety of CFPANE formulations can be made; these include topical, transdermal, transmucosal, parenteral compositions in fluid- forms i.e., solutions, suspensions, emulsions, and fine- disperse forms such as foams, liposomes, vesicles, micelles and aerosols. Known pharmaceutical excipients appropriate to the specific administration mode and use-form can be blended with CFPANE.

EXAMPLES

Group A. Examples of processes for: (a) preparation of the Symphytum plant materials to be extracted and (b) the preparation including refining (filtration/concentration/purification) of CFSYME.

Example A1. Peri- Harvest Treatment Protocol 1012

This is a process of peri-harvest conditioning/treatment/handling of the plant materials i.e., leaves, stems and/or roots, of Symphytum species which preserves their bioactive agents against evaporation, chemical degradation and photochemical interactions in the time interval between harvest and initiation of the extraction contact including the steps of:
(a) by visual inspection and other chemical/microbiological tests, selecting zones of the production field which contain Symphytum plants which have reached an optimum level of maturity (peri-bloom stage) and are essentially free of disease and have no significant levels of undesirable materials/bacteria (e.g., pyrrolozidine alkaloids) or adventitious contaminants,
(b) treating selected zones of plants to be harvested with solutions containing for example viable *Lactobacillus planterum* which can reduce the numbers of undesirable adventitious bacteria such as *E. coli* or Klebsiella,
(c) charging the harvested plant tissue immediately (within a time period of 10– 50 minutes) into a closed handling chamber which prevents exposure to sunlight, provides a controlled vapor environment to accomplish controlled dessication, including zero water removal, and to cools the plant tissue to a selected temperature in the range 250–300 deg. K, and
(d) transferring the collected plant tissue into specialized extraction apparatus for additional processing.

Example A2. Commmminution And Liquid-Fluid Extraction Process for Concentrated Fluid Symphytum Extracts This is a method of comminuting/extracting freshly-harvested plant tissue of Symphytum species which includes the steps:
(a) receiving collected plant tissue from an enclosed in-field collection/processing apparatus (see Example A1 above),
(b) comminuting the plant tissues to small pieces (avg. length or thickness dimension approx. 1 mm) by known processes such as chopping or shearing,
(c) charging the comminuted plant tissue into a closed reactor adapted to provide controlled ranges of internal pressure, temperature and forced- convection- contact-velocity differential within a time interval of 2–6 hours after receipt,
(d) charging the reactor with a liquid or liquid- mixture extracting fluid such as alcohol or water or glycerol or mixtures of these components at a selected temperature in the range between 15–55 deg. C,
(e) contacting the enclosed plant tissues under sealed environmental conditions for a time of 2 to 100 hours, preferably 4–8 at a pressure of 50–200 kPa, with controlled mechanical agitation by means of blades, or a rotating/tumbling reactor chamber, and
(f) treating the extract mixture (fluid and solids) by one or more mechanical separation methods such as sedimentation, centrifugation, filtration, etc., to separate the solid matter. Additional diatomaceous-earth filtration treatment of pre-treated liquid from prior steps may be used to remove color bodies.

Example A3. Preservation Technics For CFSYME For the case of liquid- fluid aqueous extract solutions (from Example A2 above) which must be stored for extended periods in a bulk tank (to prevent growth of microbes) by either: (a) adding a small amount (0.001 to 1.0 wt. %) of one or more chemical preservatives such as methyl and propyl paraben, or blends thereof, or (b) dewatering the active CFSYME to a dry- powder form by vacuum evaporation, spray drying, freeze drying, Example A4. Multi-Species CF Extracts - Simultaneous Extraction of Plant Tissue From Two or More Different Species Having Synergistic Bioactive Agents, e.g., Symphytum and Aloe.

This method is used for one-step preparation of extracts with two or more complimentary bioactive species. The therapeutic effects can be modulated by adjusting the mass ratio of the two respective types of tissue, the extract fluids, and processing parameters. For topical wound-healing preparations, duplex extracts with bioactive agents from two species, Symphytum and Aloe, are useful. For other conditions, ternary or quarternary one-step extracts may be of significant therapeutic value. Alternatively, tissues from more than one sub-species of the same group may be extracted simultaneously, e.g., *S. peregrinum* and *S. tauricum*.

Example A5. Process Dessication And Cryopreservation Process for Symphytum Plant Tissue This is a cryopreservation process for freshly-harvested Symphytum plant tissue to be stored for extraction at a future time which includes the steps of:

(a) removing water from the plant tissue to reduce water content to 25 wt. % or less, by vacuum drying in 3 stages at a tissue temperature of 250 deg. K. Freshly-harvested cells or tissue particles, about 1 mm size, are flash frozen to prevent cell-membrane rupture due to ice-crystal growth. Time may range from 0.1 to 10 hours depending upon the flow rate through the comminuted tissue, and (b) charging the resulting frozen plant tissue into sealed, radiation- impervious containers at a temperature in the range of 20–250 deg. K along with an inert, controlled atmosphere such as an inert gas or fluorocarbon which prevents chemical degradation of the active constituents.

Example A6. Adventitious Fungal Infection and Innoculation of Plant Tissue.

Plant tissue to be extracted may be naturally infected with adventitious yeasts/fungii due to local-environment factors or selected fungii may be administered analogous to Example A1. above, in order to produce a state of controlled infection of the tissue. Relative to cultured cells, such as callous, selected fungii may be added to the medium so that its toxins are harvested along with the medium.

Group B. Examples of different O/W—emulsion formulations which contain CFSYME, e.g., ointment, salve, lotion, cream, spray, infusion fluids, etc. In these examples, the CF Symphytum Extract is dissolved into the indicated quantity of carrier solution or base such as water, glycerol, or known drug excipient.

Example B1. Water- Based CF Symphytum Extract Solution

| A. Water Phase | | |
|---|---|---|
| CFSYME | 2–20 grams | |
| distilled water | 1000 grams | |
| methyl paraben | 1 gram | |
| propyl paraben | 0.5 gram | |

Example B2. DH100 formulation

| | | % by weight |
|---|---|---|
| A. Water Phase | | |
| methyl paraben | 17.0 grams | 0.102% |
| propyl paraben | 8.5 grams | 0.051% |
| triethanolamine | 903. grams | 5.433% |
| bacteriostat | 152. grams | 0.914% |
| deionized or distilled water | 9375. grams | 56.402% |
| CF Symphytum ext. in glycerol | 2340. grams | 14.078% |
| B. Oil Phase | | |
| stearic acid | 600. grams | 3.611% |
| glyceryl monostearate | 1575. grams | 9.476% |
| cetyl alcohol | 840. grams | 5.054% |
| olive oils | 320. grams | 1.925% |
| castor oil | 230. grams | 1.384% |
| jojoba oil | 230. grams | 1.384% |
| myrrh oil | 30. grams | 0.180% |
| peppermint oil | 1.25 grams | 0.008% |
| | 16,621.75 grams | |

C. Heat both phases to 73° C. pour A into B while mixing to form a W/O/W emulsion. Continue mixing until the temperature of the mixture is 65° C. or less.

Example B3. SCP100 formulation

| | | % by weight |
|---|---|---|
| A. Water Phase | | |
| CF Symphytum Ext. in glycerol, or deionized or distilled water | 624. grams | 13.675% |
| | 3250. grams | 71.225% |
| bacteriostat | 50. grams | 1.096% |
| methyl paraben | 5. grams | .111% |
| propyl paraben | 2.5 grams | .055% |
| diazolidinyl urea | 10.5 grams | .230% |
| B. Oil Phase | | |
| stearic acid | 144. grams | 3.156% |
| cetyl | 208. grams | 4.558% |
| olive oil | 54. grams | 1.183% |
| castor oil | 34. grams | .745% |
| jojoba oil | 34. grams | .745% |
| myrrh oil | 10. grams | .219% |
| polyoxyethylene (2) stearyl ether | 34. grams | .745% |
| polyoxyethylene 21 stearyl ether | 103. grams | 2.257% |
| | 4,653. grams | |

C. Heat both phases to 73° C. Pour A into B while mixing to form a W/O/W emulsion. Continue mixing until the temperature of the mixture is 50° C. or less.

Example B4. DC102 formulation

| | | % by weight |
|---|---|---|
| A. Water Phase | | |
| methyl paraben | 1. grams | .100% |
| propyl paraben | 0.2 grams | .020% |
| CF Symphytum Ext. in glycerol | 150. grams | 14.851% |
| bacteriostat | 10. grams | .990% |
| sodium ascorbate | 10. grams | .990% |
| polysorbate 80 | 10. grams | .990% |
| deionized water | 576. grams | 57.030% |
| B. Oil Phase | | |
| stearic acid | 40. grams | 3.960% |
| glyceryl monostearate | 105. grams | 10.396% |
| steryl alcohol | 56. grams | 5.544% |
| liquid petrolatum | 52. grams | 5.149% |
| | 1,010. grams | |

C. Heat both phases to 73° C. While mixing add B into A to form an W/O/W emulsion. Continue mixing until the temperature of the mixture is 50° C. or less.

Example B5. DC139 formulation

| | | % by weight |
|---|---|---|
| A. Water Phase | | |
| methyl paraben | 20. grams | .100% |
| propyl paraben | 4. grams | .020% |
| CF Symphytum Ext. in glycerol | 2953. grams | 14.794% |
| bacteriostat | 204. grams | 1.022% |
| polysorbate 80 | 200. grams | 1.002% |
| deionized or distilled water | 11,520. grams | 57.713% |
| B. Oil Phase | | |
| stearic acid | 800. grams | 4.008% |

-continued

|  | | % by weight |
| --- | --- | --- |
| glyceryl monostearate | 2100. grams | 10.521% |
| steryl alcohol | 1120. grams | 5.611% |
| liquid petrolatum | 1040. grams | 5.210% |
|  | 19,961. grams | |

C. Heat both phases to 73° C. Pour B into A while mixing to form an O/W emulsion. Continue mixing until the temperature of the mixture is 50° C. or less.

Example B6. SCP293 formulation

|  | | % by weight |
| --- | --- | --- |
| A. Water Phase | | |
| methyl paraben | 20. grams | .097% |
| propyl paraben | 12. grams | .058% |
| CF Symphytum Ext. in glycerol | 3084. grams | 14.980% |
| bacteriostat | 202. grams | .980% |
| triethanolamine | 400. grams | 1.900% |
| distilled water | 15,000. grams | 72.880% |
| B. Oil Phase | | |
| stearic acid | 268. grams | 1.300% |
| glyceryl monostearate | 700. grams | 3.400% |
| cetyl alcohol | 374. grams | 1.820% |
| olive oil | 214. grams | 1.040% |
| castor oil | 168. grams | .820% |
| jojoba oil | 100. grams | .490% |
| myrrh oil | 40. grams | .190% |
| peppermint oil | 1.25 grams | .006% |

C. Heat both phases to 73° deg. C Pour A into B while agitating to form a water-in-O/W emulsion. Continue mixing until the temperature of the mixture drops below 50° C.

From 0.5–5.0 wt. % of *Melaleuca uncinata* oil (frequently called Tea Tree oil) can be added to any of the examples (B1 to B6 above) for the purpose of inhibition of fungal growth at a dermal application site e.g., athlete's foot treatment, applied between toes.

Group C. Examples of non- emulsion CF Symphytum Extract pharmaceutical formulations i.e., single-phase solutions, vesicles, liposome, micelles, aerosols, tablets, microcapsules, caplets, injectable fluids, transdermal delivery patch/ device, etc.

Example C1. Isotonic Liposome Formulation LS141

Isotonic liposomes are desirable for application of CFSYME to sensitive tissue, wounds, mucous membrane, or as an ingredient in an injectable, implantable, or inhalable preparation.

Use water phase from example B1 above; adjust the solution osmolality to physiologic range (250–350 mOsm/kg) by the addition of concentrates containing physiologic salts, glucose, etc.. Form the liposome by adding the solution to a dry film of lipid such as lecithin or cholesterol; use sonication if needed.

Example C2. Aerosol Formulations A293

Aerosol formulations are of particular value in application of CFSYME to hairy areas of human or animal bodies.

In order to prepare lyophilized solid forms of CF Symphytum Extract, the extraction stage would be done with a minimal amount of water or alcohol to facilitate dewatering by evaporation, spray drying or freeze drying. Solid aerosols can be used with pressurized propellants in devices which meter and disperse the dry particles into a gas-type aerosol which may be inhaled for treatment of nasal membranes.

For liquid dispersions, a known vesicle- or emulsion-stabilizing agent is dissolved into a volatile, biocompatible propellant- solvent such as R-12 fluorocarbon. The resulting fluid is packaged into a pressurized propellant spray device to facilitate direct external application to scalp, skin or mucosal tissue.

Example C3. Transdermal/Transmucosal CFSYME Formulation A291

CFSYME such as Example B1 above are blended with known skin adhesive compounds to produce a diffusion-controlled drug delivery reservoir. Additional selected therapeutic agents may also be added for specific functions such as: (a) low levels of DMSO for enhancing the rate of absorption of the Symphytum healing agents into the skin, or (b) or synergistically increasing the healing properties of the CFSYME e.g., blending CFSYME with D-alpha-tocopherol in transmucosal adhesive devices.

Example C4. Microencapsulated formulations M 17–19

Dry- powder forms of CFSYME such as Example B1 dewatered by the process of Example A3(b), are encapsulated as microspheres (0.01 to 1.0 mm diam.) within thin, polymeric membranes using known spray- drying technics. These forms can be used for controlled release in transdermal, transmucosal, enteral, or parenteral preparations.

D. Examples of selected methods of using various formulations of CFSYME (see Groups A., B. and C. above).

Example D1. Adhesive patch for delivering controlled amounts/rates (skin, mucous membrane). Aqueous emulsion CFSYME is added during the preparation of a known hydrogel adhesive for use on human skin so that the resulting cast layer or film serves as a reservoir matrix and a diffusion- controlled delivery means for the active agents of the extract.

Example D2. Conductive electrode adhesive formulations with CF Symphytum Extract (TENS, long-term EKG monitoring, iontophoresis, etc.).

One frequent complication of transdermal electrostimulation for the relief of pain is a skin rash which develops in the tissue layers subject to the effects of allergy to the electrode material itself, the current pulses and the allergy to conductive electrode gels/creams used to reduce skin contact impedance. Similarly, electrocardiac monitoring apparatus, such as a Holter monitor, and iontophoresis devices also can produce painful skin rashes. CFSYME are blended into the conductive paste or the skin adhesive to alleviate these conditions (see Example D1 above).

Example D3. Impregnated tampon for delivering selected CF Symphytum Extract dosage to intravaginal membranes. An emulsion formulation such as Example B2 with Tea-Tree oil addition is used. Alternatively, a liposomal formulation such as Example C1 is used; by the addition of a binding ligand or antibody specific for the critical fungal vector e.g., Candida albicans, to the vesicle surface, the vesicles is targeted directly toward the infectious process.

Example D4. Microencapsulated or dry- powder aerosol forms of CFSYME such as Example C2. is administered by known metering aerosol devices for the treatment of throat or nasal irritations/inflamations which may occur in accident situations involving poison-gas attacks, fires, explosions, and exposures to irritating chemical vapors/mists.

Example D5. Liquid aerosol or liposome forms of CFSYME is administered by a spray dispenser for scalp treatment e.g., sunburn or hair-loss. For enhanced hair-growth stimulation, CFSYME are blended into known compounds. Similarly, for the treatment of aging and skin wrinkles, CFSYME are blended with compounds which are known to improve the elastic tone and thickness of the skin layer structure; for such conditions, a known acoustic or ultrasonic device is used along with the application to accelerate absorption into the skin.

Example D6. Wax-type suppository for colitis treat. CFSYME are blended into a known suppository vehicle prior to forming the suppository device.

Example D7. CFSYME for Treating Skin Conditions Related to HIV Virus Study 2303-10 patients, formulation of Example B2 used for about 6 months for eczema, folliculitis, and dry itchy skin.

RESULTS: About half the patients indicated symptomatic relief and requested additional supplies of the formulation for continuing use.

Example D8. CFSYME for Treating Skin Lesions Related to Kaposi's Sarcoma (KS) in HIV Population Study 1011- Small-group test of formulation of Example B2. Used for KS skin wounds/eruptions.

RESULTS: Formulation cleared up most skin problems and closed spots.

Example D9. CFSYME for Skin Problems In Diabetes Population Study 805. Group of 98 diabetes patients used formulation in Example B6 over a period of about 30 days for treatment of dry skin and other diabetes-related skin complications. Written evaluation instrument given to each participant to mail in at the completion of the test period. For the preliminary report, the data on 39 questionnaire responses was analyzed.

RESULTS: About 87% of the respondents indicated that the formulation was satisfactory or very satisfactory for the relief of dry-skin complications.

EXAMPLE E. Therapeutic Validation of CFTAXE in Mammals

Known in-vivo testing methods can be used to evaluate the cytotoxic and cell-proliferation-inhibition effectiveness of CFTAXE, e.g., subcutaneous injections, murine animal model, daily dose range 0.01 to 1 ml/kg of active agents based upon total body weight or the specific organ weight. In-vitro testing methods for CFTAXE include inhibition of murine monocyte activation. It is believed that the cytocidal mechanism is similar to that of other alkaloids, i.e., inhibition of the formation of microtubules in tumor cells.

On the basis of confirmation by such lab tests and animal studies, it is expected that CFTAXE formulations are useful in treating mammalian adenocarcinomas and tumors of specific organs such as the kidney, liver, pancreas, breast, colon, prostate and esophagus. Various sterile- fluid formulations/vehicles/excipients may be used for parenteral administration of CFTAXE, including single- phase solutions, emulsions, suspensions, foams, or liposomes. Using known methods for controlled release or volume blending, CFTAXE formulations can be added to IV solutions. It is believed that CFTAXE formulations also potentiate or enhance the mammalian immune response through various interactions including inhibition of protein kinase C.

EXAMPLE F. Therapeutic Validation of CFALOE in Mammals

On the basis of confirming lab tests and animal studies, it is expected that CFALOE formulations are useful in many topical compositions for treating skin dryness, irritation, burns, abrasions sensitization to skin electrodes and other conditions. CFALOE may be used with significant benefit along with CFSYME in many of the topical formulations.

EXAMPLE G. Additional Therapeutic Formulations of CFSYME, CFTAXE, and CFALOE For Mammals.

CFSYME, CFTAXE, and CFALOE medicaments described above may be further modified by the addition of one or more of the following general types of agents: antibiotics, analgesics, enzymes (such as elastase, collagenase, lipase), steroids (such as hydrocortisone), vitamins (such as A, B, C, E), hormones, biotin cofactors, emollients (such as lanolin), immunoglobulins, vaccines and other immumologic agents. Since CFSYME and CFALOE preparations may be synergistic for certain refractory skin conditions, duplex formulations containing both extacts are useful in therapy.

The preceeding examples of this invention can be repeated with similar success by substituting the generically or specifically described reagents for those used in the examples.

From the examples presented and previous descriptions, one skilled in the art can easily ascertain the essential characteristics of this invention, and without departing from the spirit and scope thereof, can make various changes and modifications of the invention to adapt it to various starting materials, body-healing usages and administration forms/ conditions.

We claim:

1. A process for preparation of concentrated fluid therapeutic extracts, cfte, by extracting bioactive components from plant tissue comprising the following steps:

(a) selecting live, healthy plants or vital cultured tissue from one or more wild or non-wild chemotaxonomically-classified plant species from the group consisting of:

*Agauria salicifolia, Albizia amara, Allium sativum, Anemarrhena asphodeliodes, Archangelica officinalis, Artemenisia annua, Artemisia annua, Aster scaber, Azadirachta indica, Bixa orellana, Bryophyllium pinnatum, Bupleuri radix, Calophyllum lanigerum, Calubrina* (mabi), *Camellia sinesis* (green tea), *Cassia alata, Coccinia indica, Dallium guincese, Desmos chinensis,* Eleutherococcus, *Eleutherococcus senticosus, Ephedra sinica, Erythrina costaricensis, Fusarium acuminatum, Galphimia glauca, Gardeniae fructus, Ginko bilboa, Glycrrhizae radix, Himanthalia elongata, Hypericum perforatum, Ipomoea tricolor, Jatropha curcas, Kigelia pinnata, Lactocuccus lactis, Lathyrus sativus, Ledum palustre, Lepechinia hastata, Mentha arvensis, Mirabilis jalapa, Momordica charantia, Notopterygium forbesii, Notopterygium incisium, Ocimum gratissimum, Origanum cordifolium, Panax japonicum, Panax japonicus, Panax notoginseng, Panax quinquefolium, Panax shinseng, Parietaria judaica, Phoenix dactylifera, Phyllanthrus amarus, Phyllanthrus maderapatensis, Picrorhiza kurroa, Piper methysticum, Pisum sativum, Plumbago rosea, Policias fruticosum* (Dihn-lang), *Pongamia pinnata, Psidium guajava, Rhododendron luteum, Rhododendron ponticum, Rosmarinus officinalis, Salvia officinalis, Saraka asoca, Slavia miltiorrhzia, Symphytum officinale, Symphytum asperum, Symphytum armeniacum, Symphytum tauricum, Symphytum sylvaticum, Symphytum peregrinum, Symphytum anatolicum, Symphytum icaricum, Symphytum orientale, Symphytum kurdicum, Symphytum pseudobulbosum, Symphytum uplandicum, Symphytum circinale, Symphytum ottomanum, Symphytum icaricum, Symphytum brachycalyx, Symphytum aintabicum, Symphytum longisetum, Symphytum bornmuelleri, Symphytum tuberosum, Symphytum bulbosum, Symphytum ibericum, Symphytum longipetiolatum, Taxus baccata, Taxus brevifolia, Taxus canadensis, Taxus chinesis, Taxus cuspidata, Taxus floridana, Teucrium cyprium, Teucrium divaricatum*

*canescens, Teucrium micropdioides, Veronia amygdalina,* and *Waldstenia fragarioides;*

(b) harvesting viable tissue from one or more plant parts of said selected plant species said parts selected from the group consisting of roots, rhizomes, stems, petioles, cultured tissues, leaves, needles, anthers, buds, fruit, nuts, seeds, pollen and blooms;

(c) charging said harvested viable tissues immediately into a protective, closed chamber, which is radiation-opaque, and which provides a controlled chemical and thermal environment defined by temperature, fluid composition, and total pressure to preserve said viable tissue and the bioactive agents contained therein and prevent degradation by air oxidation or photochemical processes;

(d) removing said charged viable tissue from said protective chamber and comminuting it immediately within said controlled chemical and thermal environment into a length or thickness dimension of approx. 1 mm to stimulate the development of phytoalexins;

(e) charging said comminuted parts within a time period of approximately 0–2 hours into a closed, extraction apparatus adapted to provide controlled chemical and physical environment with specific ranges of internal pressure, temperature and a forced-convection-contact-velocity differential between said comminuted parts and a poly-phase extraction fluid for an extended diffusion time;

(f) charging an extraction fluid into said extraction apparatus wherein said extraction fluid is selected from the group consisting of chemical compounds, a single phase, multiple phases, vapor solution, liquid solution, emulsion, and suspension, while the mass ratio of said extraction fluid to said comminuted plant tissue is held in the range 0.01 to 1000 wherein said extraction fluid is selected from the group consisting of (f1) single- or two- phase water;

(f2) single- or two- phase aqueous solutions with one or more biocompatible solutes;

(f3) two-phase, single-component organic solvents having a liquid and vapor phase in equilibrium;

(f4) multi-phase, multi-component biocompatible solution-emulsions with one or more dispersed liquid phases and an equilibrium vapor phase; and (f5) multi-phase, multi-component biocompatible solution-emulsions with one or more dispersed liquid phases, and a non-equilibrium vapor phase containing dispersed droplets, particles, or vesicles;

(g) extracting, by diffusional transfer, biologically active species into said extraction fluid from said comminuted plant tissue in said extraction apparatus for a total diffusion time in the range 0.1–200 hours while said forced-convection-contact-velocity differential is maintained within the range 0.5–3 meter/sec; and internal temperature is in the range 20–400 deg. K and an absolute internal pressure is in the range 1–5000 kPa;

(h) separating solid plant tissue residues from said resulting extract by physical means selected from the group consisting of solvent extraction, sedimentation, coagulation, distillation, centrifugation and filtration through microporous, adsorbent media.

2. The process of claim 1, for preparation of concentrated fluid taxus extracts, cftaxe, wherein (a) said selection step is selected from the group consisting of live, healthy plants or living, cultured plant tissue from one or more wild or non-wild chemotaxonomically-classified Taxus plant species free of Agrobacterium infection consisting of *Taxus baccata, Taxus brevifolia, Taxus canadensis, Taxus densiformia, Taxus chinesis, Taxus cuspidata, Taxus floridana, Taxus hickii, Taxus wallichiana, Taxus gem,* and *Taxus wardii,*

(b) said harvesting step is preceeded by a conditioning step comprising treating and conditioning said selected plants at a time 1–72 hours prior to harvest with fluids and sprayed agents to kill and wash off mechanical surface contaminants defined by adventitious bacteria, airborne particulate contaminants, and undesired residues of horticultural chemicals wherein said conditioning fluids and sprayed treating agents comprise aqueous solutions, or aqueous solutions- suspensions containing selected live bacteria and necessary support agents selected from the group consisting of surfactants, nutrients, preservatives and antioxidants necessary for supporting said live bacteria, (c) said extraction fluids comprise a quantity of mixed multi-phase, polar and non-polar solvents which amounts to 10–1000 times the mass of said comminuted plant tissue defined by one or more equilibrium or non-equilibrium liquid or vapor phases each of which is free of additives selected from the group consisting of dimethyl ether, chlorinated hydrocarbons and monohydric, primary alcohols with less than 3 carbon atoms, and (d) said diffusional transfer extracting step comprises injecting said extraction fluids at a temperature of 20–400 deg. K at a pressure of 10–1000 kPa greater than the vessel pressure as a spray with a average forced-convection-contact-velocity-differential of 0.5–3 meter/sec for a total diffusion time in the range 0.2–100 hours at temperatures in the range 20–400 deg. K and an absolute internal vessel pressure in the range 1–5000 kPa.

3. The process of claim 2, for preparation of concentrated fluid taxus extracts, cftaxe, wherein the extraction fluid is a an multi-phase aqueous solution containing up to 0.01 wt. % of a know pharmaceutical surfactant and the total diffusion time consists of a single cycle of 100–200 hours duration at 300–400 deg. K, 10–1000 kPa, and a forced convection contact velocity differential of 0.1–3 meter/sec.

4. The process of claim 2, for preparation of concentrated fluid taxus extracts, cftaxe, wherein the extraction fluid is multi-phase purified water, the total diffusion time consists of a first cycle of 1–20 hours duration at 10– 90 kPa, 300–400 deg. K, and a forced convection contact velocity of 1–5 meter/sec followed by a second cycle of 180–200 hours duration at 100–200 kPa, 40–60 deg. C, and a forced convection contact velocity differential of 0.5–5 meter/sec.

5. A therapeutic formulation for treating tumors of mammals which comprises concentrated fluid taxus extracts, cftaxe, active agent according to claim 2, blended with pharmaceutically-acceptable vehicles, diluents, additive agents, preservatives and excipients.

6. The process of claim 1, for preparation of concentrated fluid panax extracts, cfpane, wherein (a) said selection step is limited to the group consisting of live, healthy plants, and living, cultured plant tissue selected from one or more wild or non-wild chemotaxonomically-classified Panax plant species from the group consisting of *Panax japonicum, Panax japonicus, Panax notoginseng, Panax quinquefolium* and *Panax shinseng,*

(b) said harvesting step is preceeded by a conditioning step comprising treating and conditioning said selected plants at a time 1–72 hours prior to harvest with fluids and sprayed agents to increase plant-tissue moisture level to at least 5 w/o and kill and wash off mechanical surface contaminants defined by adventitious bacteria, airborne particulate contaminants, and undesired residues of horticultural chemicals wherein said conditioning fluids and sprayed treating agents comprise aqueous solutions, or aqueous solutions-suspensions containing selected live bacteria and necessary support agents defined by surfactants, nutrients, preservatives, antioxidants necessary for supporting said live bacteria, (c) said extraction fluids comprise a quantity of mixed multi-phase, polar and non-polar solvents which amounts to 10–1000 times the mass of said comminuted plant tissue defined by one or more of equilibrium liquid, non-equilibrium liquid and vapor phases each of which is free of additive monohydric, primary alcohols with less than 3 carbon atoms, and (d) said diffusional transfer extracting step comprises injecting said extraction fluids at a temperature of 20–400 deg. K at a pressure of 10–1000 kPa greater than the vessel pressure as a spray with a average forced-convection-contact-velocity-differential of 0.5–3 meter/sec for a total diffusion time in the range 0.2–100 hours at temperatures in the range 20–400 deg. K and an absolute internal vessel pressure in the range 1–5000 kPa.

7. The process of claim 6, for preparation of concentrated fluid panax extracts, cfpane, wherein the extraction fluid is a an multi-phase aqueous solution containing up to 0.01 wt. % of a known pharmaceutical surfactant and the total diffusion time consists of a single cycle of 100–200 hours duration at 300–350 deg. K, 10–1000 kPa, and a forced convection contact velocity differential of 0.1–3 meter/sec.

8. The process of claim 6, for preparation of concentrated fluid panax extracts, cfpane, wherein the extraction fluid is multi-phase purified water, the total diffusion time consists of a first cycle of 1–20 hours duration at 1– 900 kPa, 300–350 deg. K, and a forced convection contact velocity of 1–5 meter/sec followed by a second cycle of 180–200 hours duration at 100–200 kPa, 250–325 deg. K, and a forced convection contact velocity differential of 0.5–5 meter/sec.

9. A therapeutic formulation for treating diseases and nutritional deficiencies of mammals which comprises concentrated fluid panax extracts, cfpane active agent according to claim 6, blended with pharmaceutically-acceptable vehicles, diluents, additive agents, preservatives and excipients.

10. A therapeutic formulation for treating diseases and nutritional deficiencies of mammals which comprises concentrated fluid therapeutic extracts, cfte, as active agents, prepared by (a) selecting live, healthy plants or vital cultured tissue from one or more wile or non-wild chemotaxonomically-classified plant species selected from the group consisting of:

*Agauria salicifolia, Albizia amara, Allium sativum, Anemarrhena asphodeliodes, Archangelica officinalis, Artemenisia annua, Artemisia annua, Aster scaber, Azadirachta indica, Bixa orellana, Bryophyllium pinnatum, Bupleuri radix, Calophyllum lanigerum, Calubrina (mabi), Camellia sinesis (green tea), Cassia alata, Coccinia indica, Dallium guincese, Desmos chinensis,* Eleutherococcus, *Eleutherococcus senticosus, Ephedra sinica, Erythrina costaricensis, Fusarium acuminatum, Galphimia glauca, Gardeniae fructus, Ginko bilboa, Glycrrhizae radix, Himanthalia elongata, Hypericum perforatum, Ipomoea tricolor, Jatropha curcas, Kigelia pinnata, Lactocuccus lactis, Lathyrus sativus, Ledum palustre, Lepechinia hastata, Mentha arvensis, Mirabilis jalapa, Momordica charantia, Notopterygium forbesii, Notopterygium incisium, Ocimum gratissimum, Origanum cordifolium, Panax japonicum, Panax japonicus, Panax notoginseng, Panax quinquefolium, Panax shinseng, Parietaria judaica, Phoenix dactylifera, Phyllanthrus amarus, Phyllanthrus maderapatensis, Picrorhiza kurroa, Piper methysticum, Pisum sativum, Plumbago rosea, Policias fruticosum* (Dihn-lang), *Pongamia pinnata, Psidium guajava, Rhododendron luteum, Rhododendron ponticum, Rosmarinus officinalis, Salvia officinalis, Saraka asoca, Slavia miltiorrhzia, Symphytum officinale, Symphytum asperum, Symphytum armeniacum, Symphytum tauricum, Symphytum sylvaticum, Symphytum peregrinum, Symphytum anatolicum, Symphytum icaricum, Symphytum orientale, Symphytum kurdicum, Symphytum pseudobulbosum, Symphytum uplandicum, Symphytum circinale, Symphytum ottomanum, Symphytum icaricum, Symphytum brachycalyx, Symphytum aintabicum, Symphytum longisetum, Symphytum bornmuelleri, Symphytum tuberosum, Symphytum bulbosum, Symphytum ibericum, Symphytum longipetiolatum, Taxus baccata, Taxus brevifolia, Taxus canadensis, Taxus chinesis, Taxus cuspidata, Taxus floridana, Teucrium cyprium, Teucrium divaricatum__ canescens, Teucrium micropdioides, Veronia amygdalina, and Waldstenia fragarioides;*

(b) harvesting viable tissue from one or more plant parts of said selected plant species selected from the group consisting of roots, bark, rhizomes, stems, petioles, cultured tissues, leaves, needles, anthers, budds, fruit, nuts, seeds, pollen and blooms;

(c) charging said harvested viable tissues immediately into a protective, closed chamber, which is radiation-opaque, and which provides a controlled chemical and thermal environment defined by temperature, fluid composition, and total pressure to preserve said viable tissue and the bioactive agents contained therein and prevent degradation by air oxidation or photochemical processes;

(d) removing said charged viable tissue from said protective chamber and comminuting it immediately within a protective environment similar to that in said protective closed chamber into a length or thickness dimension of approx. 1 mm to stimulate the development of phytoalexins and other bioactive compounds;

(e) charging said comminuted parts within a time period of approximately 0–2 hours into a closed, extraction apparatus adapted to provide controlled chemical and physical environment with specific ranges of internal pressure, temperature and a forced-convection-contact-velocity differential between said comminuted parts and a poly-phase extraction fluid for an extended diffusion time;

(f) charging an extraction fluid into said extraction apparatus wherein said extraction fluid is a chemical compound, a single phase, multiple phases, vapor solution, liquid solution, emulsion or a suspension, and the mass ratio of said extraction fluid to said comminuted plant tissue lies in the range 0.01 to 1000 wherein said extraction fluid is selected from the group consisting of (f1) single- or two- phase water;

(f2) single- or two- phase aqueous solutions with one or more biocompatible solutes;

(f3) two-phase, single-component organic solvents having a liquid and vapor phase in equilibrium;

(f4) multi-phase, multi-component biocompatible solution-emulsions with one or more dispersed liquid phases and an equilibrium vapor phase; and (f5) multi-phase, multi-component biocompatible solution-emulsions with one or more dispersed liquid phases, and a non-equilibrium vapor phase containing dispersed droplets, particles, and vesicles;

(g) extracting, by diffusional transfer, biologically active species into said extraction fluid from said comminuted plant tissue in said extraction apparatus for a total diffusion time in the range 0.1–200 hours while said forced-convection-contact-velocity differential is maintained within the range 0.5–3 meter/sec; and internal temperature is in the range 20–400 deg. K and an absolute internal pressure is in the range 1–5000 kPa;

(h) separating solid plant tissue residues from said resulting extract by physical means selected from the group consisting of solvent extraction, sedimentation, coagulation, distillation, centrifugation and filtration through microporous, adsorbent media, and (i) blending said resulting extract active agents with pharmaceutically-acceptable vehicles, diluents, additive agents, preservatives and excipients.

11. Therapeutic formulations according to claim 10, wherein said blending step further comprises formation of storage-stable, fine-disperse formulations selected from the group consisting of powder aerosols, liquid aerosols, colloids, micelles, vesicles, emulsions, suspensions and liposomes using pharmaceutically-acceptable technics.

12. Therapeutic formulations according to claim 11, wherein said selection step is limited to said Symphytum species.

13. Therapeutic formulations according to claim 11, wherein said selection step is limited to said Panax species.

14. Therapeutic formulations according to claim 11, wherein said selection step is limited to said Aloe species.

15. Therapeutic formulations according to claim 11, wherein said selection step is limited to said Taxus species.

* * * * *